US008263324B2

(12) United States Patent
Andreassen et al.

(10) Patent No.: US 8,263,324 B2
(45) Date of Patent: Sep. 11, 2012

(54) NUCLEIC ACID ISOLATION

(75) Inventors: Jack Andreassen, Oslo (NO); Lars Korsnes, Oslo (NO); Stine Bergholtz, Oslo (NO)

(73) Assignee: Invitrogen Dynal AS, Oslo (NO)

( * ) Notice: Subject to any disclaimer, the term of this patent is extended or adjusted under 35 U.S.C. 154(b) by 60 days.

(21) Appl. No.: 12/098,411

(22) Filed: Apr. 4, 2008

(65) Prior Publication Data

US 2008/0293035 A1 Nov. 27, 2008

Related U.S. Application Data

(63) Continuation of application No. 10/297,301, filed as application No. PCT/GB01/02472 on Jun. 5, 2001, now abandoned.

(30) Foreign Application Priority Data

Jun. 5, 2000 (GB) .................................. 0013658.0

(51) Int. Cl.
*A01N 1/02* (2006.01)

(52) U.S. Cl. .......................................................... 435/2

(58) Field of Classification Search ........................ None
See application file for complete search history.

(56) References Cited

U.S. PATENT DOCUMENTS

| | | | | |
|---|---|---|---|---|
| 4,336,173 | A | | 6/1982 | Ugelstad |
| 4,459,378 | A | | 7/1984 | Ugelstad |
| 4,654,267 | A | | 3/1987 | Ugelstad et al. |
| 5,155,018 | A | | 10/1992 | Gillespie et al. |
| 5,234,809 | A | | 8/1993 | Boom et al. |
| 5,342,931 | A | | 8/1994 | Woodard et al. |
| 5,503,816 | A | | 4/1996 | Woodard et al. |
| 5,625,054 | A | | 4/1997 | Woodard et al. |
| 5,641,628 | A | * | 6/1997 | Bianchi ............................ 435/6 |
| 5,945,525 | A | | 8/1999 | Uematsu et al. |
| 6,027,945 | A | | 2/2000 | Smith et al. |

FOREIGN PATENT DOCUMENTS

| | | |
|---|---|---|
| EP | 0106873 | 2/1984 |
| EP | 0389063 | 9/1990 |
| WO | WO90/04019 | 4/1990 |
| WO | WO91/08308 | 6/1991 |
| WO | WO91/12079 | 8/1991 |
| WO | WO94/08239 | 4/1994 |
| WO | WO 9618731 A2 * | 6/1996 |
| WO | WO98/51693 | 11/1998 |

OTHER PUBLICATIONS

Bianchi et al. Direct hybridization to DNA from small numbers of flow-sorted nucleated newborn cells. Cytometry (1987) 8:197-202.*
Merel et al. Completely automated extraction of DNA from whole blood. Clin. Chem. (1996) vol. 42, No. 8, pp. 1285-1286.*
Chen et al. Rolling and transient tethering of leukocytes on antibodies reveal specializations of selectins. Proc. Natl. Acad. Sci. USA (1997) 94:3172-3177.*
Abramson et al., "Nucleic acid amplification technologies", *Current Opinion in Biotechnologies*, vol. 4, No. 1,, 1993, 41-47.
Brinchmann et al., "Direct immunomagnetic quatification of lymphocyte subsets in blood", *Clinical & Experimental Immunology*, vol. 71, No. 1, Jan. 1988, 182-186.
Dynal Biotech, User Manual for BeadRetriever, First Edition, 2000.
George et al., "Rapid Isolation of Human Endothelial Cells from Whole Blood Using S-Endo1 Monoclonal Antibody Coupled to Immuno-Magnetic Beads: Demonstration of Endothelial Injury after Angioplasty", *Thrombosis and Haemostasis*, vol. 67, No. 1, 1992, 147-153.
Syvanen et al., "A primer-guided nucleotide incorporation assay in the genotyping of apolipoprotein E", *Genomics*, vol. 8, No. 4, Dec. 1990, 684-692.
Wahlberg et al., "Rapid detection and sequencing of specific in vitro amplified DNA sequences using solid phase methods", *Molecular and Cellular Probes*, vol. 4, Issue 4, Aug. 1990, 285-297.

* cited by examiner

*Primary Examiner* — Kenneth R. Horlick
*Assistant Examiner* — David Thomas

(57) ABSTRACT

The present invention relates to a method of isolating nucleic acid from a blood sample, said method comprising: (a) selectively isolating leucocytes from said sample by binding said leucocytes to a solid support by means of a binding partner specific for leucocytes; (b) lysing said isolated leucocytes; and (c) binding nucleic acid released from said lysed cells to said solid support. Kits for isolating nucleic acid from samples form further embodiments of the invention.

25 Claims, 2 Drawing Sheets

NUCLEIC ACID ISOLATION

CROSS-REFERENCE TO RELATED APPLICATIONS

This application is a continuation of U.S. patent application Ser. No. 10/297,301, filed Apr. 30, 2003, which is a National Stage Entry (371) of PCT/GB01/02472, filed Jun. 5, 2001, which claims priority to GB 0013658.9, filed Jun. 5, 2000, which disclosures are herein incorporated by reference.

The present invention relates to the isolation of nucleic acid from blood cells, and especially to a method for isolating DNA or RNA from such cells which combines a solid phase cell isolation step with a solid phase DNA or RNA isolation step.

The isolation of nucleic acid is an important step in many biochemical and diagnostic procedures. For example, the separation of nucleic acids from the complex mixtures in which they are often found is frequently necessary before other studies and procedures e.g. detection, cloning, sequencing, amplification, hybridisation, cDNA synthesis, studying nucleic acid structure and composition (e.g. the methylation pattern of DNA) etc. can be undertaken; the presence of large amounts of cellular or other contaminating material e.g. proteins or carbohydrates, in such complex mixtures often impedes many of the reactions and techniques used in molecular biology. In addition, DNA may contaminate RNA preparations and vice versa. Thus, methods for the isolation of nucleic acids from complex mixtures such as cells, tissues etc. are demanded, not only from the preparative point of view, but also in the many methods in use today which rely on the identification of DNA or RNA e.g. diagnosis of microbial infections, forensic science, tissue and blood typing, genotyping, detection of genetic variations etc.

The use of DNA or RNA identification is now widely accepted as a means of distinguishing between different cells or cell types or between variants of the same cell type containing DNA mutations. Thus, HLA typing, which is more commonly carried out by identification of characteristic surface antigens using antibodies, may alternatively be effected by identification of the DNA coding for such antigens. Microbial infection or contamination may be identified by nucleic acid analysis to detect the target organism, rather than relying on detecting characterising features of the cells of the microorganisms e.g. by detecting morphological or biochemical features. Genetic variations may be identified by similar means.

Particularly in the fields of nucleic acid diagnostics, population studies and genotyping, it is important to obtain high quality and pure nucleic acid preparations to ensure that further amplification and/or detection steps are reliably and accurately carried out.

Isolation of nucleic acid from blood cells is required for a number of applications, including for example typing, or for diagnostic or screening applications for example to detect mutations or polymorphisms. For such applications large amounts of pure nucleic acid, particularly genomic DNA, are desirable. Particularly, it is desirable to obtain such nucleic acid readily and speedily and to avoid the use of materials which may contaminate and/or degrade the nucleic acid.

A range of methods are known for the isolation of nucleic acids, but generally speaking, these rely on a complex series of extraction and washing steps and are time consuming and labourious to perform. Moreover, the use of materials such as alcohols and other organic solvents, chaotropes and proteinases is often involved which is disadvantageous since such materials tend to interfere with many enzymic reactions and other downstream processing applications.

Thus, classical methods for the isolation of nucleic acids from complex starting materials such as blood or blood products or tissues involves lysis of the biological material by a detergent or chaotrope, possibly in the presence of protein degrading enzymes, followed by several extractions with organic solvents e.g. phenol and/or chloroform, ethanol precipitation, centrifugations and dialysis of the nucleic acids. Not only are such methods cumbersome and time consuming to perform, but the relatively large number of steps required increases the risk of degradation, sample loss or cross-contamination of samples where several samples are simultaneously processed. In the case of RNA isolation, the risk of DNA contamination is relatively high.

Improvements in methods for isolating nucleic acids have been made, and more recently, other methods have been proposed which rely upon the use of a solid phase. In U.S. Pat. No. 5,234,809, for example, is described a method where nucleic acids are bound to a solid phase in the form of silica particles, in the presence of a chaotropic agent such as a guanidinium salt, and thereby separated from the remainder of the sample. WO 91/12079 describes a method whereby nucleic acid is trapped on the surface of a solid phase by precipitation. Generally speaking, alcohols and salts are used as precipitants.

Whilst such methods speed up the nucleic acid separation process, a need still exists for methods which are quick and simple to perform, which enable good yields to be obtained without losses, and in particular which do not require the use of solvents, alcohols and similar agents. In addition, particularly where large quantities of nucleic acid are required to be isolated, methods which are effective for large as well as small volumes of sample material are desirable.

Chaotropes require to be used at high molarity, resulting in viscous solutions which may be difficult to work with, especially in RNA work. Amplification procedures such as PCR, and other enzyme-based reactions, are very sensitive to the inhibitory or otherwise interfering effects of alcohols and other agents. Moreover, the drying of the nucleic acid pellet which is necessary following alcohol precipitation and the problems with dissolving nucleic acids, are also known to lead to artefacts in enzyme-based procedures such as PCR. Since such procedures are now a mainstay of molecular biology, there is a need for improved methods of nucleic acid isolation from blood samples, and particularly for methods which are quick and simple to perform and which avoid the use of chaotropic agents or alcohol precipitation. In addition, as it is sometimes desirable to isolate relatively large amounts of nucleic acid from blood samples, there is a need for methods which enable good yields of nucleic acid to be obtained from both large (e.g. 1 ml to 100 ml or more) and small (e.g. up to 1 ml) blood samples. There is also a need for a method which allows for differentiation between RNA and DNA and permits a separate isolation of both types of nucleic acid from the same sample. The present invention seeks to provide such methods.

In particular, it has now been found that nucleic acid may be isolated from a blood or blood-derived sample in a form suitable for amplification or other downstream processes, by a simple and easy to perform procedure which involves specifically isolating nucleic acid-containing cells from the sample onto a solid support, lysing the isolated support-bound cells and allowing the released nucleic acid to bind to the same solid support (or alternatively to bind to a mixture of the same and different solid supports), whereupon to bind to the nucleic acid may be readily separated from the sample, e.g. by removal of the support from the sample. The binding of the nucleic acid is independent of its sequence. Moreover, by appropriate choice of nucleic acid binding conditions and/or the nature of the solid support, it can be selected whether DNA or RNA binds to the support, thereby enabling a selective DNA or RNA isolation procedure.

In one aspect, the present invention thus provides a method of isolating nucleic acid from a blood sample, said method comprising:

(a) selectively isolating leucocytes from said sample by binding said leucocytes to a solid support by means of a binding partner specific for leucocytes;

(b) lysing said isolated leucocytes; and (c) binding nucleic acid released from said lysed cells to said solid support.

More particularly, in step (a), leucocytes in said sample may be bound to a leucocyte-specific binding partner, said binding partner being attached to a solid support before or after binding to said leucocytes, thereby to bind said support to said leucocytes.

The nucleic acid may be DNA, RNA or any naturally occurring modification thereof, and combinations thereof. Preferably however the nucleic acid will be DNA, which may be single or double stranded or in any other form, e.g. linear or circular. The method of the present invention is particularly suited to isolating genomic DNA.

The term "leucocyte" is used herein to include any nucleic acid-containing cell of the blood. Thus, the term "leucocyte" includes all white blood cells. Such cells may be lymphoid cells e.g. lymphocytes such as T-cells and B-cells, or natural killer (NK) cells or myeloid cells e.g. monocytes/macrophages, granulocytes/neutrophils, eosinophils, basophils/mast cells, megakaryocytes and erythroid progenitor cells. Dendritic cells (both myeloid and lymphoid) are also included. All nucleated cells which may occur in the blood or haemopoietic system are included.

The "blood sample" may be any sample derived from blood which retains cells, for example whole blood or buffy coat. The sample may be freshly obtained, or stored or treated in any desired or convenient way, for example by dilution or adding buffer, or other solutions or solvents, enzyme-containing solutions etc.), as long as the integrity of the leucocytes within it is maintained (i.e. as long as the leucocyte surface remains intact). The "blood sample" may also be any "blood-related" sample, for example a sample obtained from other haemopoietic tissues such as bone marrow, or from other tissues/fluids which may contain cells of haemopoietic origin, e.g. ascites, lymphatic fluid, or cell suspensions (e.g. single cell suspensions) obtained from any such tissues or fluids. Thus, the "blood sample" may be any haemopoietic sample or any sample (e.g. a clinical sample) containing cells of haemopoietic origin. Thus, alternatively defined, the invention can be seen to provide a method, as defined above, which is a method of isolating nucleic acid from a cell sample (e.g. a clinical sample), and in particular from such a sample containing cells of haemopoietic origin. Such a cell sample is thus a sample containing leucocytes.

Preferably samples are 10 μl to 100 ml in size, preferably from 200 μl to 10 ml. The method of the invention may be used for small samples, e.g. less than 1 ml or for larger samples e.g. at least 2 ml, e.g. more than 5 ml or 10 ml or 50 ml.

Affinity-based separation or isolation systems for desired target cells are well known in the art, and rely on the specificity of a binding partner, specific or selective for the target cell, to achieve selective isolation of the cell. Such a system is employed according to the present invention in order to achieve selective isolation of leucocytes from the sample. Thus, the binding partner in step (a) may be any moiety having a binding affinity for a leucocyte, and in particular a selective or specific binding affinity such that it binds specifically to leucocytes present in the sample but not to other cells or components of the sample.

The binding partner may be any molecule or moiety capable of binding to a leucocyte, but conveniently will be a protein, polypeptide or peptide. Other moieties or molecules of a different chemical nature, for example carbohydrates or small organic molecules may however also be used. Nucleic acid binding partners e.g. aptamers may also be used.

The binding partner may bind to molecules or structures on the surface of the leucocytes, for example to cell surface antigens which are expressed (e.g. specifically) on the surface of leucocytes. Alternatively, the binding partner may be a moiety binding to a cell surface expressed protein e.g. a cell surface receptor.

The binding partner may, for example, conveniently be an antibody specific for a leucocyte surface antigen. Antibody fragments and derivatives may also be used, according to techniques well known in the art.

Antibodies for use as binding partners in methods of the present invention may be of any species, class or subtype. Furthermore the antibody may be natural, derivatised or synthetic. Representative "antibodies" thus include:

(a) any of the various classes or sub-classes of immunoglobulin, e.g. IgG, IgA, IgM, IgD or IgE derived from any animal e.g. any of the animals conventionally used, e.g. sheep, rabbits, goats, or mice, (b) monoclonal or polyclonal antibodies (c) intact antibodies or fragments of antibodies, monoclonal or polyclonal, the fragments being those which contain the binding region of the antibody, e.g. fragments devoid of the Fc portion (e.g. Fab, Fab', $F(ab')_2$, Fv), the so called "half molecule" fragments obtained by reductive cleavage of the disulphide bonds connecting the heavy chain components in the intact antibody.

(d) antibodies produced or modified by recombinant DNA or other synthetic techniques, including monoclonal antibodies, fragments of antibodies, "humanised antibodies", chimeric antibodies, or synthetically made or altered antibody-like structures. Also included are functional derivatives or "equivalents" of antibodies e.g. single chain antibodies, CDR-grafted antibodies, minimum recognition unit antibodies etc.

Methods for preparing such fragments or derivatives are well known in the art and widely described in the literature.

In addition to antibodies or antibody-based molecules, other types of binding partner may be used, for example peptide or other molecules, synthetically made and/or selected from display or combinatorial libraries e.g. phage display. Mention may be made of aptamers. Other types of leucocyte-specific binding partner may include affibodies or other synthetic affinity molecules, and lectins.

Leucocytes may express or carry a variety of molecules on their surface which may be recognised by a specific binding partner. Such molecules may be common to all or most (e.g. substantially all) leucocytes (so-called "pan-leucocyte") or they may be carried/expressed by only a subset of leucocytes, for example particular cell types such as T-cells, B-cells, lymphocytes in general, monocytes etc. Ideally, binding partners specific for pan-leucocyte molecules or antigens are used. However, the invention permits one or more different binding partners to be used, and hence combinations or mixtures of binding partners may be used to achieve the desired separation.

Thus, a binding partner, or combination or mixture of binding partners, may be selected to achieve a desired separation or isolation of leucocytes from the sample. Advantageously, all or substantially all (i.e. close to all) leucocytes present in the sample may be separated. The separation achievable may be dependent not only on the binding partner(s) selected, but also on the nature of the sample, binding conditions etc. Also, biological systems are by their nature variable, and 100% separation may not always be achieved, and, indeed, is not necessary according to the present invention; as in any biological system, some tolerance must be allowed for. However, in preferred embodiments of the invention at least 60%, 65%, 70%, 75%, 80%, 85%, 90% or 95% of the leucocytes present in the sample may be separated.

Leucocytes express on their surface a range of molecules classified under the "CD" system and also HLA antigens, which may be used as "targets" for the leucocyte-specific binding partners. Preferred binding partners according to the invention thus include those recognising or capable of binding specifically to one or more of: HLA-I, CD11a, CD18, CD45, CD46, CD50, CD82, CD100 or CD162. CD5 and/or CD15 may also be included in this list. One or more of such binding partners may be used.

Other antigens are expressed more selectively, for example CD5 is expressed by lymphoid cells, including T- and B-cells and NK cells. CD15 is expressed by monocytes and neutrophils. HLA-I is expressed by lymphocytes but not granulocytes. Table 1 below shows other such antigens, and Table 2 shows the typical distribution of different leucocyte cell types in a blood sample. Appropriate combinations of binding partners recognising the different antigens of Table 1 may be selected to enable the desired separation of leucocytes from a sample, e.g. to isolate the majority of leucocytes from a sample.

A combination of binding partners for CD45 and CD15 represents a preferred embodiment according to the present invention.

TABLE 1

| Lymphoid cells | | Myeloid cells | |
|---|---|---|---|
| T-cell | B-cell and NK | Monocyte | Neutrophil |
| Different cell surface molecules expressed in the haematopoietic system | | | |
| CD2 | | | |
| CD3 | | | |
| CD3 + CD8 | | | |
| CD5 | CD5 | | |
| | | CD13 | CD13 |
| | | CD15 | CD15 |
| CD43 | | | CD43 |
| | | CD88 | CD88 |
| | | CD97 | CD97 |
| | | CD101 | CD101 |
| CD107a | | | CD107a |
| Different cell surface molecules expressed on all the leucocytes: | | | |
| HLA-I | HLA-I | HLA-I | HLA-I |
| CD11a | CD11a | CD11a | CD11a |
| CD18 | CD18 | CD18 | CD18 |
| CD45 | CD45 | CD45 | CD45* |
| CD46 | CD46 | CD46 | CD46 |
| CD50 | CD50 | CD50 | CD50 |
| CD82 | CD82 | CD82 | CD82 |
| CD100 | CD100 | CD100 | CD100 |
| CD162 | CD162 | CD162 | CD162 |

*CD45 does not have a very high expression on neutrophils

TABLE 2

| Distribution of different leucocytes in normal blood samples | |
|---|---|
| Cell type | % range |
| Neutrophil | 45-76% |
| Eosinophil | 2-4% |
| Basophil | 0.5-1% |
| Monocytes | 6-10% |
| Lymphocytes (T-cells 60-80%) | 20-35% |

Normally a blood sample contains $6\times10^9$ leucocytes/litre (range $2\text{-}12\times10^9$)

The solid support may be any of the well known supports or matrices which are currently widely used or proposed for immobilisation, separation etc. These may take the form of particles, sheets, gels, filters, membranes (e.g. nylon membranes), fibres, capillaries, needles or microtitre strips, tubes, plates or wells, etc, combs, pipette tips, micro arrays, chips, or indeed any solid surface material.

Conveniently the support may be made of glass, silica, latex, plastic or any polymeric material. Generally speaking, for isolation of DNA, the nature of the support is not critical and a variety of surface materials may be used. The surface of the solid support may be hydrophobic or hydrophilic. Preferred are materials presenting a high surface area for binding of the cells, and subsequently, of the nucleic acid. Such supports will generally have an irregular surface and may be for example be porous or particulate e.g. particles, fibres, webs, sinters or sieves. Particulate materials e.g. beads are generally preferred due to their greater binding capacity, particularly polymeric beads/particles.

Conveniently, a particulate solid support used according to the invention will comprise spherical beads. The size of the beads is not critical, but they may for example be of the order of diameter of at least 1 and preferably at least 2 μm, and have a maximum diameter of preferably not more than 10 and more preferably not more than 6 μm. For example, beads of diameter 2.8 μm and 4.5 μm have been shown to work well.

Monodisperse particles, that is those which are substantially uniform in size (e.g. size having a diameter standard deviation of less than 5%) have the advantage that they provide very uniform reproducibility of reaction. Monodisperse polymer particles produced by the technique described in U.S. Pat. No. 4,336,173 are especially suitable.

Non-magnetic polymer beads suitable for use in the method of the invention are available from Dynal Particles AS (Lillestrøm, Norway; previously Dyno Particles or Dyno Speciality Polymers) as well as from Qiagen, Amersham Pharmacia Biotech, Serotec, Seradyne, Merck, Nippon Paint, Chemagen, Promega, Prolabo, Polysciences, Agowa, Bangs Laboratories and Dyno Particles or Dyno Speciality Polymers.

However, to aid manipulation and separation, magnetic beads are preferred. The term "magnetic" as used herein means that the support is capable of having a magnetic moment imparted to it when placed in a magnetic field, and thus is displaceable under the action of that field. In other words, a support comprising magnetic particles may readily be removed by magnetic aggregation, which provides a quick, simple and efficient way of separating the particles following the cell and nucleic acid binding steps, and is a far less rigorous method than traditional techniques such as centrifugation which generate shear forces which may disrupt cells or degrade nucleic acids.

Thus, using the method of the invention, the magnetic particles with cells attached may be removed onto a suitable surface by application of a magnetic field e.g. using a permanent magnet. It is usually sufficient to apply a magnet to the side of the vessel containing the sample mixture to aggregate the particles to the wall of the vessel and to pour away the remainder of the sample.

Especially preferred are superparamagnetic particles for example those described by Sintef in EP-A-106873, as magnetic aggregation and clumping of the particles during reaction can be avoided, thus ensuring uniform nucleic acid extraction. The well-known magnetic particles sold by Dynal Biotech ASA (Oslo, Norway, previously Dynal AS) as DYNABEADS, are particularly suited to use in the present invention.

Functionalised coated particles for use in the present invention may be prepared by modification of the beads according to U.S. Pat. Nos. 4,336,173, 4,459,378 and 4,654,267. Thus, beads, or other supports, may be prepared having different types of functionalised surface, for example positively or negatively charged, hydrophilic or hydrophobic.

The binding partner(s) may be attached to the solid support in any convenient way, before or after binding to the leucocytes, according to techniques well known in the art and described in the literature. Thus the binding partner may be attached directly or indirectly to the solid support.

In a convenient embodiment, the binding partner may be attached to the support, prior to contact with the sample. Such attachment may readily be achieved by methods (e.g. coupling chemistries) well known in the art, and conveniently the binding partner is bound directly to the solid support, for example by coating. However it may also be attached via spacer or linker moieties. The binding partner may be covalently or reversibly attached according to choice.

Alternatively, as mentioned above, the binding partner may first be brought into contact with the sample, to bind to the leucocytes before being attached to the solid support. In this case, the solid support may conveniently carry or be provided with a binding moiety capable of binding to the leucocyte-specific binding partner. Again, such binding systems are well known in the art. For example, the solid surface may carry a (secondary) antibody capable of binding to the anti-leucocyte binding partner (e.g. a polyclonal anti-species antibody).

Where more than one different type of binding partner is used (e.g. anti-CD45 and anti-CD15 antibodies) they may be attached to the same or different solid supports. Such a system using different solid supports, is applicable particularly in the case of a particulate support such as beads. Thus, different binding partners may be attached to different beads.

In embodiments where more than one different type of binding partner is used, appropriate amounts or ratios at which the different types of binding partner may be used will be readily determined by a person skilled in the art. For example, in preferred embodiments of the present invention, where anti CD45 and anti CD15 antibodies are used, these may be used at any ratio providing that said ratio allows cells to be isolated. Preferable ratios are 1:1 and 2:1 ratios of CD45 to CD15.

As mentioned above, cell separation techniques based on solid phase affinity binding (e.g. immunomagnetic separation (IMS)) are well known in the art and conditions to achieve this may readily be determined by the skilled worker in this field. Thus, for example a solid support carrying anti-leucocyte binding partner(s) may be brought into contact with the sample. A particulate solid support may, for example, be added to the sample contained (e.g. suspended) in an appropriate medium (e.g. a buffer). The support may then be left in contact with the sample (e.g. incubated) for a length of time to enable binding to the cells to occur. Conditions during the step are not critical, and the sample-support mixture may be incubated at e.g. 4 to 20° C. for 10 minutes to 2 hours e.g. 20-45 minutes.

Following cell binding, the isolated or support-bound cells are lysed to release their nucleic acid. Methods of cell lysis are well known in the art and widely described in the literature and any of the known methods may be used. Any of the following methods could, for example, be used: detergent lysis using e.g. SDS, LiDS or sarkosyl in appropriate buffers; the use of chaotropes such as Guanidium hydrochloride (GHCl) Guanidium thiocyanate (GTC), sodium iodide (NaI), perchlorate etc; mechanical disruption, such as by a French press, sonication, grinding with glass beads, alumina or in liquid nitrogen; enzymatic lysis, for example using lysozyme, proteinases, pronases or cellulases or any of the other lysis enzymes commercially available; lysis of cells by bacteriophage or virus infection; freeze drying; osmotic shock; microwave treatment; temperature treatment; e.g. by heating or boiling, or freezing, e.g. in dry ice or liquid nitrogen, and thawing; alkaline lysis. As mentioned above, all such methods are standard lysis techniques and are well known in the art, and any such method or combination of methods may be used.

As mentioned above, the present invention affords the advantage that the use of agents such as solvents, alcohols and chaotropes may be avoided. Thus, whilst lysis methods such as those mentioned above using such agents may be employed, in advantageous embodiments of the invention the use of such agents is avoided.

Conveniently, lysis may be achieved according to the present invention by using detergents. An exemplary suitable lysis agent thus includes a detergent such as SDS or another alkali metal alkylsulphate salt, e.g. LiDS, or Sarkosyl or combinations thereof. The lysis agents may be supplied in simple aqueous solution, or they may be included in a buffer solution, to form a so-called "lysis buffer". Any suitable buffer may be used, including for example Tris, Bicine, Tricine and phosphate buffers. Alternatively the lysis agents may be added separately. Salts, for example LiCl and NaCl, may also be included in or added to the lysis buffers. In particular, LiCl is preferred when LiDS is used and NaCl is preferred when SDS is used.

Suitable concentrations and amounts of lysis agents will vary according to the precise system etc. and may be appropriately determined, but concentrations of e.g. 2M to 7M chaotropes such as GTC GHCl, NaI or perchlorate may be used, 0.1M to 1M alkaline agents such as NaOH, and 0.1 to 50% (w/v) e.g. 0.5 to 15% detergent.

To carry out the method of the invention, the isolated, support-bound cells, may conveniently be removed or separated from the remainder of the sample, thereby concentrating or enriching the cells. Thus the leucocyte binding step serves to enrich the cells or to concentrate them in a smaller volume than the initial sample. To facilitate subsequent steps, it may be desirable, prior to the lysis step, to dilute the support bound cells, e.g. in an appropriate buffer or other medium. If desired the cells may further be treated, e.g. by heating or mixing (e.g. vortexing). A dilution step may be advantageous to prevent agglomeration/aggregation of a particulate support such as beads, particularly in a genomic DNA matrix which makes further handling of the beads difficult and not reliable for transfer of the supernatant or the bead pellet to another compartment or receptacle e.g. well/tube/tray etc. Lysis then may conveniently be achieved by adding an appropriate lysis buffer containing the desired lysis agents or by subjecting the isolated cells to the desired lysis conditions. For example, in the case of simply adding a lysis buffer containing appropriate lysis agents, the isolated cells may simply be incubated in the presence of the lysis buffer for a suitable interval to allow lysis to take place. Different incubation conditions may be appropriate for different lysis systems, and are known in the art. For example for a detergent containing lysis buffer, incubation may take place at room temperature or at higher temperatures e.g. 37° C., 50° C. or 65° C. Likewise, time of incubation may be varied from a few minutes e.g. 5 or 10 minutes to hours, e.g. 20 to 40 minutes or 1 to 2 hours. For enzymatic lysis, e.g. using proteinase K etc, longer treatment times may be required, e.g. overnight.

In an advantageous embodiment of the invention the lysis step of the method comprises a further step involving the addition of a further or extra amount of solid support to the isolated leucocytes. Such "further" solid support (also referred to herein as a "second" solid support) may comprise the same or a different solid support from that used in step (a) of the method and may be added to the cell sample as a separate component before or after the addition of the lysis buffer or be included in the lysis solution or buffer. The further or second solid support may thus comprise any of the solid supports discussed above for use in step (a). However, as the isolation of the leucocytes has already been carried out by the lysis stage, there is no absolute requirement for the second solid phase to have a leucocytes specific binding partner associated with its surface. The use of a second solid support has been found to offer advantages in sample collection for example by improving pellet formation and hence isolation of the first solid support. The improved pellet formation may also reduce non-specific binding of substances or entities in the pellet, or in other words reduces contamination of the pellet. Whilst not wishing to be bound by theory it is believed that when only a first solid support is used the isolated nucleic acid binds to the first solid support as a loose, non-compact mesh, thereby resulting in a relatively loose non-compact pellet. However, where a second support is used and particularly when this second solid support comprises particles which are smaller or larger than the first solid support, the second solid support fills in the gaps (or vice versa) in the loose mesh, thereby making the pellet tighter and more compact thus reducing the tendency to trap contaminating material.

Thus the second solid support may be of comparable size and density to the first solid support. Preferably however, the second solid support is of a smaller size than the first solid support. For example, where the supports are particulate the second solid support comprises particles of a smaller diameter (e.g. approximately half the diameter), than those comprising the first solid support. In especially preferred embodiments the first solid support comprises particles of 4.5 μm diameter (e.g. the M450 beads described herein) whereas the second solid support comprises particles of 2.8 μm diameter (e.g. the M280 and M270 beads described herein). Alternatively, the first support may be smaller than the second support and the dimensions described above may be reversed.

Especially preferably the second solid support may take a more active role in the isolation of the nucleic acid and in such cases the second solid phase is capable of binding to nucleic acid, i.e. has nucleic acid binding properties. Preferably therefore the second solid support may be made of glass, silica, latex, plastic or any polymeric material (i.e. an uncoated surface) capable of binding nucleic acid and such a solid support may optionally be functionalised, for example to aid or improve nucleic acid binding. Particularly preferred in this regard are functionalised solid supports which have a surface charge, preferably a negative surface charge. Most preferred are solid supports coated with carboxylic acid functional groups. Such solid supports are commercially available, for example the M-270 carboxylic acid beads or M-280 Hydroxyl beads manufactured by Dynal Biotech ASA. Preferably the second solid supports are particulate, e.g. beads, and especially preferably are magnetic.

The provision of a further or extra amount of solid support after the cell isolation step results in an improved yield of nucleic acid and also makes the elution of nucleic acid from the solid support easier, particularly where solid supports with a negatively charged surface are used. Whilst not wishing to be bound by theory, as described above it is believed that the addition of an extra amount of a "second" solid support improves the compactness of the bead and nucleic acid pellet and particularly where DNA is able to bind to the second solid support, more effective and complete binding of nucleic acid molecules, rather than the nucleic acid molecules being attached to the beads only at one end or being attached to the beads loosely is achieved.

Thus, a further embodiment of the invention provides a method of isolating nucleic acid from a blood sample, said method comprising:

(a) selectively isolating leucocytes from said sample by binding said leucocytes to a first solid support by means of a binding partner specific for leucocytes;

(b) lysing said isolated leucocytes;

(c) binding nucleic acid released from said lysed cells to said first solid support; and (d) contacting said isolated leucocytes of step (b) or the nucleic acid of step (c) with an additional amount of a second solid support, preferably binding said nucleic acid to said second solid support which is capable of binding nucleic acid.

Preferably the isolated lymphocytes are lysed in the presence of said second solid support.

This method using a second solid support can equally be used to selectively isolate nucleic acid from cells in any sample. In such methods, the cells from which it is desired to isolate nucleic acid are selectively isolated from the sample by binding said cells to a first solid support by means of one or more appropriate binding partners, after which steps (b), (c) and (d) of the method described above are carried out on the particular isolated cells in question.

Appropriate first and second solid supports for use in such methods are discussed herein (and may be the same or different), as are appropriate methods for the selective isolation of cells and methods of lysis. Preferably the lysis step (b) of the method also involves the use of proteinases and in particular proteinase K at an appropriate concentration. As discussed above, the use of proteinases in conventional techniques of nucleic acid isolation is often disadvantageous since such materials tend to interfere with many enzymic reactions and other downstream processing applications. However, in preferred methods of the present invention these disadvantageous effects of proteinases are minimised by the use of magnetic separation technology wherein the amount of contaminating enzymes will be negligible as the beads are moved from vial to vial during the isolation of nucleic acid and subsequent washing steps.

The terms "additional" or "extra" or "further" amount when used herein in connection with the addition of a second solid phase, is used to indicate the addition of any amount (by weight) of second solid phase such that the isolation of nucleic acid is improved, for example the yield of isolated nucleic acid is improved. For example the amount of second solid phase added might be the same amount as the amount of first solid phase used or may be up to approximately 3 to 5 times the amount of first solid phase used. Alternatively, the amount of second solid phase added may be less than the amount of first solid phase providing that the isolation of nucleic acid is improved. Preferably the amount of second solid phase used is 0.5 to 3 times the amount of first solid phase.

As the "amount" of solid phase refers to the weight of the solid phase, in the preferred embodiments of the invention where the first and second solid phases are particulate and the particles making up the second solid phase are smaller (or larger) than the particles making up the first solid phase, the number of particles used for the first and second solid phases will generally be different.

Following lysis, the released nucleic acid is bound to the same support to which the lysed cells are bound or in other embodiments of the invention the released nucleic acid is bound to the same solid support to which the lysed cells are bound and the additional second solid support. This nucleic acid binding may be achieved in any way known in the art for binding nucleic acid to a solid support. Conveniently, the nucleic acid is bound non-specifically to the support i.e. independently of sequence. Thus, for example the released nucleic acid may be precipitated onto the support using any of the known precipitants for nucleic acid, e.g. alcohols, alcohol/salt combinations, polyethylene glycols (PEGs) etc. Precipitation of nucleic acids onto beads in this manner is described for example in WO 91/12079. Thus, salt may be added to the support and released nucleic acid in solution, followed by addition of alcohol which will cause the nucleic acid to precipitate. Alternatively, the salt and alcohol may be added together, or the salt may be omitted. As described above in relation to the cell binding step, any suitable alcohol or salt may be used, and appropriate amounts or concentrations may readily be determined. However, as mentioned above, it is preferred to avoid the use of solvents, alcohols and similar agents. Thus alternative techniques, avoiding the use of such agents are preferred.

One such alternative and preferred nucleic acid-binding technique includes the use of detergents as described in WO 96/18731 of Dynal AS (the so-called "DNA Direct" procedure). Various detergent-based systems for binding nucleic acids to a solid support are described in this publication and may be used according to the present invention.

Conveniently, the nucleic acid binding step may take place simultaneously or concomitantly with the cell lysis step. This may conveniently be achieved using the detergent-based methods of WO96/18731. Thus, for example, an agent or agents for lysis and nucleic acid binding may conveniently be contained in an appropriate medium (e.g. a buffer or other aqueous solution) and added to the support-bound cells. The cells may then be maintained in contact with the medium e.g. incubated (e.g. as described above) to allow lysis and nucleic acid binding to take place. Such a medium may be referred to as a "lysis/binding" medium. A detergent may function as both lysis agent and to assist in the binding of the nucleic acid to the support.

The detergent may be any detergent, and a vast range are known and described in the literature. Thus, the detergent may be ionic, including anionic and cationic, non-ionic or zwitterionic. The term "ionic detergent" as used herein includes any detergent which is partly or wholly in ionic form when dissolved in water. Anionic detergents have been shown to work particularly well and are preferred. Suitable anionic detergents include for example sodium dodecyl sulphate (SDS) or other alkali metal alkylsulphate salts or similar detergents, sarkosyl, or combinations thereof.

Conveniently, the detergent may be used in a concentration of 0.2 to 30% (w/v), e.g. 0.5 to 30%, preferably 0.5 to 15%, more preferably 1 to 10%. For anionic detergents concentrations of 1.0 to 5% e.g. 0.5 to 5% have been shown to work well.

The detergent may be supplied in simple aqueous solution, which may be alkaline or acidic, or more preferably in a buffer. Any suitable buffer may be used, including for example Tris, Bicine, Tricine, and phosphate buffers. Conveniently, a source of monovalent cations, e.g. a salt, may be included to enhance nucleic acid capture, although this is not necessary. Suitable salts include chloride salts, e.g. sodium chloride, lithium chloride etc. at concentrations of 0.1 to 1M, e.g. 250 to 500 mM. As mentioned above, other components such as enzymes, may also be included.

Other optional components in the detergent composition include chelating agents e.g. EDTA, EGTA and other polyamino carboxylic acids conveniently at concentrations of 1 to 50 mM etc., reducing agents such as dithiotreitol (DTT) or β-mercaptoethanol, at concentrations of for example 1 to 10 mM.

Preferred detergent compositions may for example comprise:

100 mM Tris-HCl pH 7.5
10 mM EDTA
2% SDS or:

100 mM Tris Cl pH 7.5
10 mM EDTA
5% SDS
10 mM NaCl or:

100 mM Tris Cl pH 7.5
500 mM LiCl
10 mM EDTA
1% LiDS

Reference is made to WO96/18731 for further details, exemplary reaction conditions etc.

In the embodiments of the invention where a second solid support is added, this second solid support may be included in the detergent composition. Further preferred detergent compositions thus comprise the above compositions further comprising an appropriate amount of second solid support, e.g. M270 carboxylic acid beads or M-280 Hydroxyl beads, for example at a concentration of approximately 1.5 mg/ml and optionally an appropriate amount of proteinases, e.g. proteinase K, for example at 20 mg/ml.

By selecting appropriate "nucleic acid binding" conditions (e.g. appropriate buffer or lysis/binding medium compositions), it may be selected whether to bind DNA released from the cells, or RNA released from the cells to the solid support. Thus, "binding medium" compositions may be selected favouring DNA binding (or more particularly genomic DNA binding) to the solid support. Such binding medium compositions include those mentioned above, those described in the Examples below, and the compositions of WO96/18731. For example, a representative DNA binding medium may include GuHCl and optionally EDTA.

To bind RNA, appropriate medium compositions or conditions are known in the art, or may readily be determined from RNA isolation procedures known in the art, and may include, for example, the buffers and procedures described in EP-A-0389063 and U.S. Pat. No. 5,234,809 of Akzo Nobel NV.

Representative RNA-binding compositions may thus include guanidine thiocyanate (GTC) with EDTA.

For RNA binding, the nature of the solid support may be of importance and in particular a "silica" (i.e. comprising silica itself or being based on silica or a silica derivative) solid surface should be used (see further below)

Advantageously, when the method of the invention is used to isolate DNA, it may be combined with a further step separately to isolate the RNA from the sample. Thus, following the procedure discussed above, and selecting DNA-binding conditions in the nucleic acid binding step (e.g. a lysis/binding or binding medium favouring DNA binding), DNA released from the support-bound cells may be bound to the support, and removed from the sample. RNA, most notably mRNA, released from the leucocytes, remains in the sample (more precisely in the supernatant). This RNA may readily be isolated from the sample using standard procedures, for example by binding to a capture probe, conveniently immobilised (e.g. by binding to a solid support), consisting of oligo dT.

Alternative nucleic acid binding techniques may also be used in order to achieve the step of binding released nucleic acid to the solid support. For example, one such method may take advantage of the well known principle of nucleic acid binding to a silica surface.

Thus, in such an embodiment, the solid support may comprise or consist of a silica or silica-based or derived material. Many such materials are known and described in the art, and the literature is replete with references describing the isolation of nucleic acids by binding to silica surfaces (see e.g. EP-A-0389063 of AKZO N.V., U.S. Pat. No. 5,342,931, U.S. Pat. No. 5,503,816 and U.S. Pat. No. 5,625,054 of Becton Dickinson, U.S. Pat. No. 5,155,018 of Hahnemann University, U.S. Pat. No. 6,027,945 of Promega Corp. and U.S. Pat. No. 5,945,525 of Toyo Boseki KK).

Ionic binding of the nucleic acid to the support may be achieved by using a solid support having a charged surface, for example a support coated with polyamines.

The support which is used in the method of the invention may also carry functional groups which assist in the specific or non-specific binding of nucleic acids, for example DNA binding proteins e.g. leucine zippers or histones or intercalating dyes (e.g. ethidium bromide or Hoechst 42945) which may be coated onto the support.

Likewise, the support may be provided with binding partners to assist in the selective capture of nucleic acids. For example, complementary DNA or RNA sequences, or DNA binding proteins may be used. The attachment of such proteins to the solid support may be achieved using techniques well known in the art. Conveniently, such nucleic acid-binding partners may be intermixed on the solid support with the anti-leucocyte binding partners.

Although not necessary, it may be convenient to introduce one or more washing steps to the isolation method of the invention, for example following the cell isolation and/or nucleic acid binding step. Any conventional washing buffers or other media may be used. Generally speaking, low to moderate ionic strength buffers containing salt are preferred e.g. 10 mM Tris-HCl at pH 8.0/10 μM or 40 mM NaCl. Other standard washing media, e.g. containing alcohols, may also be used, if desired, for example washing with 70% ethanol.

The use of magnetic particles permits easy washing steps simply by aggregating the particles, removing the nucleic acid binding medium, adding the washing medium and reaggregating the particles as many times as required.

Following the nucleic acid isolation process and any optional washing steps which may be desired, the support carrying the bound nucleic acid may be transferred e.g. resuspended or immersed into any suitable medium e.g. water or low ionic strength buffer. Thus, the isolated nucleic acid may be removed or separated from the sample. Depending on the support and the nature of any subsequent processing desired, it may or may not be desirable to release the nucleic acid from the support.

In the case of a particulate solid support such as magnetic or non-magnetic beads, this may in many cases be used directly, for example in PCR or other amplifications, without eluting the nucleic acid from the support. Also, for many DNA detection or identification methods elution is not necessary since although the DNA may be randomly in contact with the bead surface and bound at a number of points by hydrogen bonding or ionic or other forces, there will generally be sufficient lengths of DNA available for hybridisation to oligonucleotides and for amplification.

However, if desired, elution of the nucleic acid may readily be achieved using known means, for example by heating, e.g. to 65° C. for 5 to 10 minutes, following which the support may be removed from the medium leaving the nucleic acid in solution. Such heating is automatically obtained in PCR by the DNA denaturation step preceding the cycling program. An elution buffer not containing salt may also conveniently be used.

If it is desired to remove RNA from DNA, this may be achieved by destroying the RNA before the DNA separation step, for example by addition of an RNAase or an alkali such as NaOH.

An advantage of the present invention, is that it is quick and simple to perform, and with an appropriate combination of cell-binding, lysis and nucleic acid binding steps, provides a method which reliably and simply yields isolated nucleic acid in a short period of time, in many cases, less than one hour, or even less than 45 minutes. The simplicity of the method allows for high throughput of samples. Concomitantly, the cell-binding step, results in an enrichment or concentration of the cells, and purification away from other components in the sample, thereby improving the nucleic acid isolation process. Advantageously also, the use of solvents such as chloroform/phenol is avoided. Advantageously, the method of the invention permits nucleic acid to be isolated from relatively small samples of blood, for example up to 10 ml of blood, for example 10 μl to 2 ml of blood, e.g. 200 to 500 μl of blood or 50 to 200 μl, (e.g. 100 μl) of buffy coat. The yields and quality of nucleic acid isolated using the methods of the invention are good. For example 0.2 ml of blood routinely provides 5-12 μg DNA with an $OD_{260/280}$ ratio of 1.75-1.9. In addition, as mentioned above, the methods of the invention can be used to isolate nucleic acid from large samples of blood, e.g. from samples of greater than 10 mls.

Particularly favourable results have been obtained using the method of the invention to isolate genomic DNA from blood samples. In particular, it has been shown that high quality DNA may be obtained, with little fragmentation.

The invention is advantageously amenable to automation, particularly if particles, and especially, magnetic particles are used as the support. In a particularly favoured embodiment of the invention, the nucleic acid isolation method is performed using an automated system for handling of the solid support during the cell lysis, nucleic acid binding, and, optionally, washing steps. Thus the isolated support-bound cells may be transferred to such an apparatus, washed if desired, and lysed;

the nucleic acid may bind to the support, and the bound nucleic acid may readily be washed, using such an apparatus. Furthermore, such an apparatus may also be used to handle the support during the cell isolation stage. Particular mention may be made in this regard of the Bead Retriever™, available from Dynal ASA, Norway. The apparatus has a system for ready and efficient transfer of the support (carrying cells or nucleic acid) from one well to another. Such an apparatus is particularly efficacious in handling the high quality viscous DNA which results from the method of the invention.

As mentioned above, the method of the invention has particular utility as a preliminary first step to prepare nucleic acid for use in nucleic acid-based detection procedures, for example in genotyping.

As mentioned above, advantageously the bound nucleic acid need not be eluted or removed from the support prior to carrying out the detection step, although this may be performed if desired. Whether or not the nucleic acid is eluted may also depend on the particular method which was used in the nucleic acid binding step. Thus certain nucleic acid-binding procedures will bind the nucleic acid more tightly than others. In the case of DNA-binding using detergents (e.g. by DNA Direct) for example, the nucleic acid will elute from the solid support when an elution buffer or other appropriate medium is introduced. Nucleic acid bound by means of a precipitant such as alcohol or a chaotrope will remain more tightly bound and may not elute when placed in a buffer medium, and may require heating to be eluted.

Thus, the support-bound nucleic acid may be used directly in a nucleic acid based detection procedure, especially if the support is particulate, simply by resuspending the support in, or adding to the support, a medium appropriate for the detection step. Either the nucleic acid may elute into the medium, or as mentioned above, it is not necessary for it to elute.

A number of different techniques for detecting nucleic acids are known and described in the literature and any of these may be used according to the present invention. Conveniently, nucleic acid may be detected by optical methods, for example by measuring or determining optical density (OD). Alternatively, the nucleic acid may be detected by hybridisation to a probe and very many such hybridisation protocols have been described (see e.g. Sambrook et al., 1989, Molecular Cloning: A Laboratory Manual, 2nd Ed. Cold Spring Harbor Press, Cold Spring Harbor, N.Y.). Most commonly, the detection will involve an in situ hybridisation step, and/or an in vitro amplification step using any of the methods described in the literature for this. Thus, as mentioned, techniques such as LAR, 3SR and the Q-beta-replicase system may be used. However, PCR and its various modifications e.g. the use of nested primers, will generally be the method of choice (see e.g. Abramson and Myers, 1993, Current Opinion in Biotechnology, 4: 41-47 for a review of nucleic acid amplification technologies).

Other detection methods may be based on a sequencing approach, for example, the minisequencing approach as described by Syvänen and Söderlund, 1990, Genomics, 8: 684-692.

In amplification techniques such as PCR, the heating required in the first step to melt the DNA duplex may release the bound DNA from the support. Thus, in the case of a subsequent detection step, such as PCR, the support bound nucleic acid may be added directly to the reaction mix, and the nucleic acid will elute in the first step of the detection process. The entire isolated support bound nucleic acid sample obtained according to the invention may be used in the detection step, or an aliquot.

The results of the PCR or other detection step may be detected or visualised by many means, which are described in the art. For example the PCR or other amplification products may be run on an electrophoresis gel e.g. an ethidium bromide stained agarose gel using known techniques. Alternatively, the DIANA system may be used, which is a modification of the nested primer technique. In the DIANA (Detection of Immobilised Amplified Nucleic Acids) system (see Wahlberg et al., Mol. Cell. Probes 4: 285 (1990)), the inner, second pair of primers carry, respectively, means for immobilisation to permit capture of amplified DNA, and a label or means for attachment of a label to permit recognition. This provides the dual advantages of a reduced background signal, and a rapid and easy means for detection of the amplified DNA.

The amplified nucleic acid may also be detected, or the result confirmed, by sequencing, using any of the many different sequencing technologies which are now available, e.g. standard sequencing, solid phase sequencing, cyclic sequencing, automatic sequencing and minisequencing.

Advantageously, it has been found that isolated cells may be kept in a “cell-binding” buffer according to the invention e.g. a salt/alcohol buffer for at least one week at room temperature with no detectable loss of sensitivity in a subsequent nucleic acid detection step. Such stability is an advantage in field situations.

Thus, the methods of the invention may be used to isolate nucleic acid for any appropriate subsequent use. Examples of such uses are described briefly above. Advantageously the methods of the invention could be used to prepare and isolate nucleic acid from samples at the point of care, e.g. at or near the patient’s bed-side or in a doctor’s surgery, where the nucleic acid isolated or obtained could then optionally be used in down-stream testing also at the point of care, e.g. could be used in yes/no gene testing in for example a dot hybridization assay.

The various reactants and components required to perform the methods of the invention may conveniently be supplied in kit form. Such kits represent a further aspect of the invention.

At its simplest, this aspect of the invention provides a kit for isolating nucleic acid from a sample comprising:

(a) a solid support;

(b) means for binding leucocytes to said solid support;

(c) means for lysing said cells; and (d) means for binding nucleic acid released from said lysed cells to said same solid support.

Further optional components of the kit include (e) a second solid support, which may be the same or different to the solid support component (a), and (f) a proteinase such as Proteinase K. In the kits of the invention where a second solid support is included it should be noted that such kits can equally be used to isolate nucleic acid from any cell sample and are not limited to isolating nucleic acid from a sample containing leucocytes, e.g. a blood sample. In such kits, component (b) is replaced by an appropriate means for binding the particular cells from which it is desired to isolate nucleic acid to a solid support.

The various means (b), (c), (d), (e) and (f) may be as described and discussed above, in relation to the methods of the invention.

A further optional component is (g), means for detecting the nucleic acid. As discussed above, such means may include appropriate probe or primer oligonucleotide sequences for use in hybridisation and/or amplification-based detection techniques.

Optionally further included in such a kit may be buffers, salts, polymers, enzymes etc.

The invention will now be described in more detail in the following non-limiting Examples with reference to the drawings in which.

EXAMPLE 1

General Protocol for Isolation of DNA from Leucocytes

We have developed a method for isolation and purification of DNA from specifically isolated cells, namely leucocytes, from blood. The method is based on the use of antibodies or other affinity molecules coated on a solid support, such as magnetic beads for specific cell isolation. Subsequent lysis of these cells, in an appropriate medium e.g. in a buffer with salt or chaotrope containing a detergent, releases the DNA and the DNA adsorbs to the beads. RNA and other contaminants remain in the supernatant and by separation of the support, e.g. magnetically, the DNA/support complex is washed to remove these residual contaminants. The DNA is then resuspended in an appropriate buffer and is ready to be used in downstream applications.

Leucocyte Isolation

375 μg each of magnetic M450 CD45 and M450 CD15 Dynabeads™ (available from Dynal ASA) provided with anti-CD45 or anti-CD15 antibody, (resuspended in PBS, pH 7.4, with 0.1% BSA and 0.02% $NaN_3$) in a ratio of 1:1 are washed and resuspended in DPBS (Dulbecco's PBS (phosphate buffered saline) used without $Ca^{2+}$ and $Mg^{2+}$), pH 7.4, with 0.1% BSA and 0.6% NaCitrate. The beads are then added to blood or buffy coat and incubated for 20-45 minutes at 4-20° C. The cells are isolated magnetically and washed in DPBS, pH 7.4, with 0.1% BSA and 0.6% NaCitrate or added directly to Lysis/binding buffer (see Cell lysis) without washing.

Cell Lysis

The beads with the isolated cells attached added to Lysis/Binding buffer (100 mM Tris-HCl, pH 7.5, 100 mM LiCl, 10 mM EDTA, pH 8.0, 1% LiDS and 5 mM DTT (dithiothreitol)) and incubated for five minutes at room temperature.

Washing and Elution

The DNA/bead complex is isolated magnetically and washed in 40 mM NaCl. The DNA is eluted in 10 mM Tris-HCl pH 7.4 by vigorous pipetting and subsequent incubation at 65° C. for 5 minutes. The beads are magnetically removed from the eluted DNA.

EXAMPLE 2

Automated Isolation of Genomic DNA from Buffy Coat

In this procedure, both cell isolation and DNA isolation steps are automated.

DNA isolation from 100 μl buffy coat, diluted to 1 ml with DPBS, pH 7.4, with 0.1% BSA and 0.6 k NaCitrate, was performed using 375 μg M450 CD45 and 375 μg M450 CD15.

Figure 1:
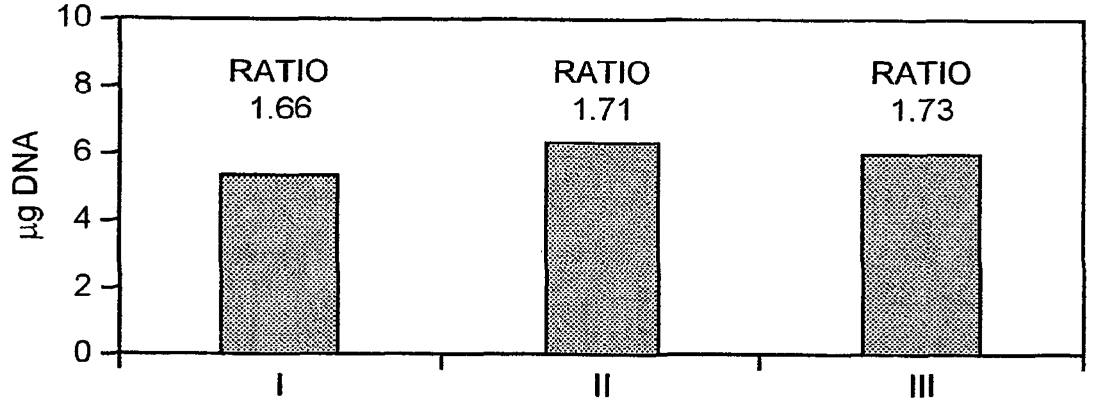
FIG. 1 is a chart showing yield of DNA (μg) isolated from a 100 μl buffy coat sample as described in Example 2, isolations I, II and III.

Both isolation of cells and DNA was performed by using the Dynal BeadRetriever™ apparatus. The isolated cells were transferred to Lysis/Binding buffer and the DNA/bead complex was washed twice in 40 mM NaCl before partial elution in 10 mM Tris-HCl pH 7.4. To elute the DNA completely vigorous pipetting and elution at 65° C. was performed manually. The DNA yield was determined by measuring the $OD_{260}$ and $OD_{280}$ and by using the Warburg-Christian formula ([Nucleic Acid, μg/ml]=62.9 $OD_{260}$−36.0 $OD_{280}$). The purity of the isolated DNA was determined by the ratio $OD_{260}/OD_{280}$ where a ratio between 1.7 and 2.0 is considered as a pure DNA preparation. The results are shown in Table 3 below, and also in FIG. 1.

TABLE 1

| Parallel | $OD_{280}$ | $OD_{280}$ | Ratio 260/280 | Volume μl | μg/ml DNA | μg/DNA |
|---|---|---|---|---|---|---|
| I | 0.758 | 0.457 | 1.66 | 170 | 31.23 | 5.31 |
| II | 0.778 | 0.456 | 1.71 | 189 | 32.56 | 6.15 |
| III | 0.792 | 0.459 | 1.73 | 180 | 33.29 | 5.99 |

EXAMPLE 3

Semi-Automated Isolation of Genomic DNA for Buffy Coat

In this procedure, cells are isolated manually and DNA isolation is automated.

Figure 2:
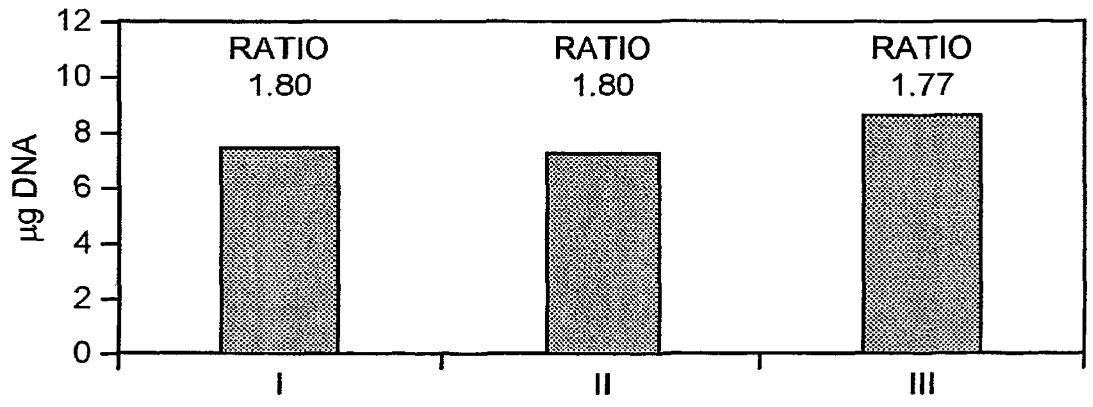
FIG. 2 is a chart showing yield of DNA (μg) isolated from a 100 μl buffy coat sample as described in Example 3, isolations I, II and III.

DNA isolation from 100 μl buffy coat, diluted to 300 μl with DPBS, pH 7.4, with 0.1% BSA and 0.6% NaCitrate, was performed using 375 μg M450 CD45 and 375 μg M450 CD15. Isolation of cells was performed manually and DNA isolation was performed by using the Dynal BeadRetriever™. The manually isolated cells were washed three times before addition of Lysis/Binding buffer. The DNA/bead complex was washed three times in 40 mM NaCl before partial elution in 10 mM Tris-HCl pH 7.4. To elute the DNA completely vigorous pipetting and elution at 65° C. was performed manually. The DNA yield was determined by measuring the $OD_{260}$ and $OD_{280}$ and by using the Warburg-Christian formula ([Nucleic Acid, μg/ml]=62.9 $OD_{260}$−36.0 $OD_{280}$). The purity of the isolated DNA was determined by the ratio $OD_{260}/OD_{280}$ where a ratio between 1.7 and 2.0 is considered as a pure DNA preparation. The results are shown in Table 4 below, and also in FIG. 2.

TABLE 4

| Parallel | $OD_{260}$ | $OD_{280}$ | Ratio 260/280 | Volume μl | μg/ml DNA | ug DNA |
|---|---|---|---|---|---|---|
| I | 0.942 | 0.522 | 1.80 | 186 | 40.46 | 7.53 |
| II | 0.834 | 0.463 | 1.80 | 205 | 35.79 | 7.34 |
| III | 1.104 | 0.624 | 1.77 | 180 | 46.98 | 8.46 |

EXAMPLE 4

DNA Isolation from Blood Using Beads with Both CD45 and CD15 Compared to Beads with CD45 and CD15 on Two Different Beads Cells were isolated from 1 ml whole blood samples (containing approximately $2.10^7$ leucocytes) using the general procedure described in Example 1. Beads carrying both anti-CD45 and anti-CD15 (KB 458-18; KB 458-16 and KB 458-10; these designations represent different bead preparations) were compared to a procedure using a combination of separate CD45 and CD15 beads (as in previous Examples). 375 µg of beads were used in each case.

The number of leucocytes in 1 ml of blood was determined by flow cytometry to be 2,600,000. Blood samples were diluted from 9.6 ml to 12.5 ml, namely a 1.3× dilution, thereby resulting in 2,000,000 leucocytes. Assuming 5 pg DNA per cell gives an estimate of DNA in 1 ml of blood of 12 µg.

Figure 3:
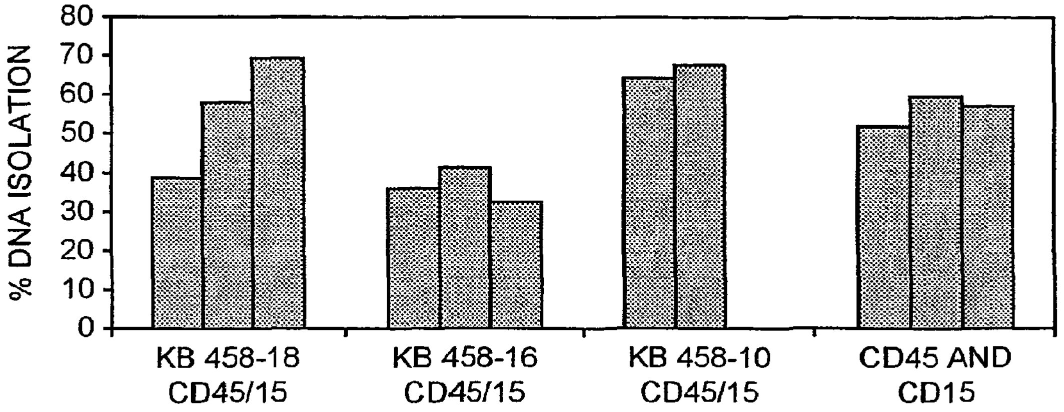
FIG. 3 is a chart showing % of DNA isolated from a 1 ml blood sample as described in Example 4, using different antibody-bead preparations (CD45/CD15 beads: KB 458-18; KB 458-16; and KB 458-10; and separate CD45 and CD15 beads).

The results obtained are shown in Table 5 and in FIG. 3.

TABLE 5

| | Parallel | $OD_{260}$ | $OD_{280}$ | $OD_{320}$ | Ratio | Volume | µg/ml DNA | ug DNA | % of theoretical |
|---|---|---|---|---|---|---|---|---|---|
| KB458- | 1 | 0.766 | 0.471 | 0.081 | 1.76 | 157 | 29.05 | 4.6 | 38.00 |
| 18 | 2 | 1.117 | 0.752 | 0.155 | 1.61 | 180 | 39.02 | 7.0 | 58.53 |
| | 3 | 1.334 | 0.901 | 0.21 | 1.63 | 180 | 45.82 | 8.2 | 68.74 |
| KB458- | 4 | 0.597 | 0.35 | 0.048 | 1.82 | 180 | 23.66 | 4.3 | 35.49 |
| 16 | 5 | 0.836 | 0.55 | 0.136 | 1.69 | 170 | 29.13 | 5.0 | 41.26 |
| | 6 | 0.559 | 0.338 | 0.051 | 1.77 | 178 | 21.62 | 3.8 | 32.07 |
| KB458- | 7 | 1.216 | 0.815 | 0.185 | 1.64 | 182 | 42.17 | 7.7 | 63.96 |
| 10 | 8 | 1.161 | 0.736 | 0.142 | 1.72 | 190 | 42.17 | 8.1 | 67.63 |
| | 9 | | | | | | 0.00 | 0.0 | 0.00 |
| CD45 | 10 | 0.934 | 0.581 | 0.09 | 1.72 | 175 | 35.41 | 6.2 | 51.64 |
| CD15 | 11 | 1.054 | 0.654 | 0.096 | 1.72 | 181 | 40.17 | 7.3 | 60.59 |
| | 12 | 0.961 | 0.587 | 0.082 | 1.74 | 185 | 37.11 | 6.9 | 57.21 |

No. WBC in 1 ml blood (determined by flow): 2,600,000
Blood diluted from 9.6 to 12.5 ml - 1.3x diluted: 2,000,000
6 pg DNA pr. cell gives ug DNA 1 ml blood = 12

EXAMPLE 5

General Protocol for Isolation of DNA from Leucocytes Using the Dynal BeadRetriever™

Materials:

Blood

M450 CD45 and M450 CD15 or M450 CD45/15

DPBS/BSA (0.1% BSA og 0.6% NaCitrate)

(50 ml DPBS+250 µl 20% BSA+30 mg NaCitrate)

Lysis/Binding buffer (100 mM Tris-HCl, pH 7.5, 500 mM NaCl, 10 mM EDTA, pH 8, 0.5 mM DTT, 1% SDS)

Washing buffer (40 mM NaCl)

10 mM Tris-HCl ph 7.4

DPBS=Dulbecco's PBS used without $Ca^{2+}$ and $Mg^{2+}$

DTT=Dithiothreitol

Method:

Isolation and Washing of Leucocytes:

1. Use $1.10^7$ beads per 1 ml blood. The beads are either 1:1 M450 CD45 and CD15 or M450 CD45/15.
2. Remove the supernatant and wash the beads with DPBS/BSA buffer.
3. Add the beads to 2 ml tubes with screw cap.
4. Add 1 ml blood. Mix carefully but well by pipetting.
5. Incubate 20 min at 2-8° C. on a roller.
6. To the rack of tubes for BeadRetriever add:
   Tube 1—empty (to add the 1 ml blood with isolated cells)
   Tube 2, 3, 4 and 5—1 ml DPBS/BSA
7. After cell isolation, add the blood with the isolated cells in the first tube of the BeadRetriever tube rack.
8. Put the tubes and tips in the BeadRetriever and start the program:
   Tube 1—collect isolated cells
   Tube 2, 3 and 4 wash 1 min
   Tube 5—wash 1 min, collect cells on tips and put in position 0

Lysis, Binding of DNA and Washing in BeadRetriever:

9. To a new rack of tubes for BeadRetriever add:
   Tube 1—500 µl Lysis/Binding buffer
   Tube 2, 3 and 4—1 ml Washing buffer
   Tube 5—200 µl 10 mM Tris-HCl pH 7.4
10. Leave the tips in the machine, but replace the tubes from cell washing with the new tubes for DNA binding and washing.
11. Start the program:
    Tube 1—5 min lysis
    Tube 2, 3 and 4—1 min washing
    Tube 5—vigorous shaking to release the bead complex Elution and Determination of DNA Purity and Yield:

12. DNA will not be released during shaking in the BeadRetriever and needs to be handled manually. Transfer everything in tube 5 to an Eppendorf tube and pipette up and down several times until the beads are in solution.
13. Elute the DNA at 65° C. for 5 min. Transfer the supernatant to a new tube.
14. Determine the $OD_{260}$, $OD_{280}$ and $OD_{320}$. Calculate the ratio:

($OD_{280}$ and $OD_{320}$)/($OD_{280}$ and $OD_{320}$)

15. Calculate the amount of DNA isolated:

µg DNA=[62.9*($OD_{260}$ and $OD_{320}$)−36.0*($OD_{280}$ and $OD_{320}$)]*ml elution volume 16. Run 5 µl sample on an agarose gel to visualise the size an amount of DNA.

EXAMPLE 6

DNA Isolation from Leucocytes Using Both a First and a Second Solid Support

Material

Blood

M450 CD45 ($4\times10^8$ beads/ml and 30 mg/ml)

M450 CD15 ($4\times10^8$ beads/ml and 30 mg/ml)

DPBS with 0.1% BSA

Lysis/Binding buffer (100 mM Tris-HCl, pH 7.5, 500 mM LiCl, 10 mM EDTA, pH 8.0, 0.5 mM DTT, 1% LiDS) with 1.5 mg/ml M270-COOH 20 mg/ml Proteinase K Washing buffer (10 mM Tris pH 8.0, 150 mM LiCl)

Resuspension buffer (Tris-HCl pH 8.0, 0.01% Tween-20)

Methods

Isolation and Washing of Leukocytes:

1. Use $6\times10^6$ beads (450 μg) per 200 μl blood in a ratio of 2:1 of M450 CD45 and CD15. Remove the supernatant and wash the beads with DPBS/BSA buffer.
2. Add the washed beads to 200 μl blood diluted in 200 μl DPBS/BSA buffer. Mix carefully but well by pipetting.
3. Incubate with constant movement for 20 minutes at room temperature.
4. Wash the isolated cells three times in DPBS/BSA buffer. Change the tube at the first wash. Remove the supernatant.

Lysis of Leukocytes and Isolation of DNA

5. Add 0.5 ml lysis/binding buffer containing 1.5 mg/ml extra beads and 20 μl of 20 mg/ml Proteinase K to the isolated cells and beads. Do not mix by pipetting.
6. Incubate for 5 minutes at room temperature with constant movement.
7. Wash three times by adding washing buffer without further pipetting.
8. Add 200 μl resuspension buffer and incubate for 5 minutes at 80° C.
9. Spin shortly, pipette a few times and/or flick the tube. Transfer the supernatant to a new tube.

Determination of DNA Purity and Yield:

10. Determine the $OD_{260}$, $OD_{280}$, $OD_{320}$. Calculate the ratio: $(OD_{260}-OD_{320})/(OD_{280}-OD_{320})$.
11. Calculate the amount of DNA isolated:

$$\mu g\ DNA=[50\times(OD_{260}-OD_{320})]\times ml\ elution\ volume.$$

Figure 4:
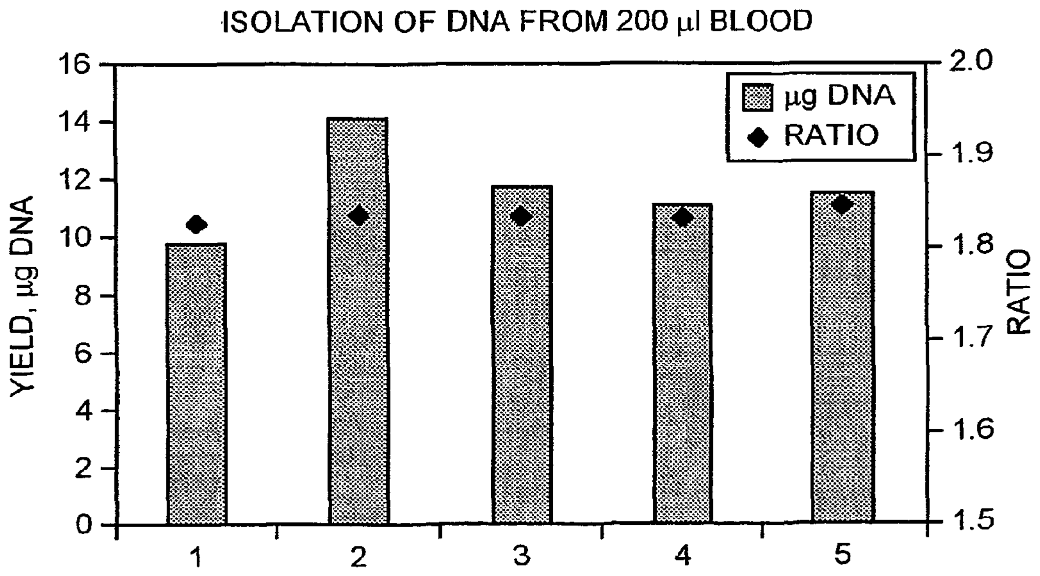
FIG. 4 is a graph showing the yield of DNA (μg) isolated from 200 μl of blood as described in Example 6. The value of a ratio giving an indication of DNA purity as described in Example 6 is also shown (♦).

The results from five different blood samples which have been taken through this protocol are shown in FIG. 4.

The invention claimed is:

1. A method of isolating nucleic acid from a blood sample, said method comprising:

(a) selectively isolating leucocytes from said sample by binding said leucocytes to a first solid support by means of at least two different binding partners specific for leucocytes;

(b) lysing said isolated leucocytes;

(c) binding nucleic released from said lysed leucocytes to said first solid support; and (d) contacting the nucleic acid of step (c) with an additional amount of a second solid support, and binding the nucleic acid to said second solid support;

wherein the method is performed using an automated system for handling the first solid support and second solid support during cell lysis, nucleic acid binding or both, and wherein the first solid support and second solid support are transferred from a first tube to a second tube by the automated system, wherein the at least two different binding partners recognize or are capable of binding specifically to CD45 and CD15, and wherein the first solid support comprises polymeric particles.

2. The method of claim 1 wherein in step (a), said binding partners are attached to a solid support before or after binding to said leucocytes, thereby binding said support to said leucocytes.

3. The method of claim 1 wherein the nucleic acid is DNA, RNA or any naturally occurring modification thereof, or combinations thereof.

4. The method of claim 1 wherein the different binding partners in step (a) bind specifically to leucocytes present in the sample but not to other cells or components of the sample.

5. The method of claim 4 wherein said different binding partners are antibodies or fragments or derivatives of antibodies.

6. The method of claim 1 wherein all or substantially all leucocytes present in the sample are separated.

7. The method of claim 1 wherein said solid support is superparamagnetic.

8. The method of claim 1 wherein the different binding partners are attached directly or indirectly to the solid support of step (a).

9. The method of claim 8 wherein said different binding partners are attached to the same or different solid support.

10. The method of claim 9 wherein the nucleic acid binding in step (c) is carried out using a detergent based system.

11. A method of isolating nucleic acid from a cell sample, said method comprising:

(a) selectively isolating cells from said sample by binding said cells to a first solid support by means of at least two different binding partners specific for said cells;

(b) lysing said isolated cells;

(c) binding nucleic acid released from said lysed cells to said first solid support; and (d) contacting the nucleic acid of step (c) with an additional amount of a second solid support, and binding said nucleic acid to said second solid support;

wherein the method is performed using an automated system for handling of the first solid support and second solid support during cell lysis, nucleic acid binding or both, and wherein the first solid support and second solid support are transferred from a first tube to a second tube by the automated system, wherein the at least two different binding partners recognize or are capable of binding specifically to CD45 and CD15, and wherein the first solid support comprises polymeric particles.

12. The method of claim 11 wherein the cells are leucocytes.

13. The method of claim 11 wherein the cell sample is a blood sample.

14. The method of claim 11 wherein the first solid support comprises at least two different binding partners that recognize or are capable of binding specifically to one or more of the molecules selected from the group comprising HLA-I, CD11a, CD18, CD45, CD46, CD50, CD82, CD100, CD162, CD5 and CD15 and the second solid support, which is different from said first solid support, is negatively charged.

15. The method of claim 11 wherein said automated system additionally handles the support during the cell isolation stage.

16. The method of claim 11 wherein in step (a), said binding partners attach to a solid support before or after binding to said leucocytes.

17. The method of claim 11 wherein the nucleic acid is DNA, RNA or any naturally occurring modifications thereof, or combinations thereof.

18. The method of claim 11 wherein the different binding partners in step (a) binds specifically to leucocytes present in the sample but not to other cells or components of the sample.

19. The method of claim 11 wherein said different binding partners are antibodies or fragments or derivatives of antibodies.

20. The method of claim 11 wherein all or substantially all leucocytes present in the sample are separated.

21. The method of claim 11 wherein said solid support is superparamagnetic.

22. The method of claim 11 wherein the different binding partners are attached directly or indirectly to the solid support of step (a).

23. The method of claim 22 wherein said different binding partners are attached to the same or different solid support.

24. The method of claim 11 wherein the nucleic acid binding in step (c) is carried out using a detergent based system.

25. The method of claim 11 wherein the nucleic acid of step (c) is additionally contacted with an additional amount of a second solid

* * * * *